(12) United States Patent
Nienhuis

(10) Patent No.: US 8,696,038 B2
(45) Date of Patent: Apr. 15, 2014

(54) FLAT BOTTOM FITTING ASSEMBLY

(75) Inventor: Nathaniel Nienhuis, Oak Harbor, WA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 0 days.

(21) Appl. No.: 13/411,352

(22) Filed: Mar. 2, 2012

(65) Prior Publication Data

US 2013/0227831 A1    Sep. 5, 2013

(51) Int. Cl.
*F16L 19/06* (2006.01)

(52) U.S. Cl.
USPC ........... 285/385; 285/342; 285/353; 285/384; 210/198.2; 210/656

(58) Field of Classification Search
USPC ............... 285/342, 343, 353, 385, 384, 389; 210/198.2, 656
See application file for complete search history.

(56) References Cited

U.S. PATENT DOCUMENTS

| | | | | |
|---|---|---|---|---|
| 1,497,453 A * | 6/1924 | Levitt | | 285/343 |
| 2,127,611 A * | 8/1938 | Mueller | | 285/342 |
| 2,182,811 A * | 12/1939 | Kocher | | 285/342 |
| 2,523,874 A * | 9/1950 | Moore | | 285/342 |
| 3,498,647 A * | 3/1970 | Schroder | | 285/343 |
| 3,582,115 A * | 6/1971 | Clague | | 285/341 |
| 3,676,573 A * | 7/1972 | Avery | | 285/341 |
| 3,695,640 A * | 10/1972 | Clague | | 285/341 |
| 3,893,716 A * | 7/1975 | Moreiras et al. | | 285/341 |
| 4,043,576 A * | 8/1977 | Reich et al. | | 285/342 |
| 4,136,897 A * | 1/1979 | Haluch | | 285/342 |
| 4,138,145 A | 2/1979 | Lawrence | | |
| 4,235,461 A * | 11/1980 | Normark | | 285/341 |
| 4,309,050 A * | 1/1982 | Legris | | 285/342 |
| 5,472,598 A | 12/1995 | Schick | | |
| 5,525,303 A | 6/1996 | Ford et al. | | |
| 5,730,943 A | 3/1998 | Ford et al. | | |
| 6,095,572 A | 8/2000 | Ford et al. | | |
| 7,316,777 B2 * | 1/2008 | Loy, Jr. | | 285/343 |
| 7,789,433 B2 * | 9/2010 | Calnek | | 285/353 |
| 8,201,854 B2 * | 6/2012 | Ford et al. | | 285/385 |
| 2006/0169628 A1 | 8/2006 | Loy | | |
| 2012/0014848 A1 | 1/2012 | Ellis et al. | | |
| 2012/0024411 A1 | 2/2012 | Hahn et al. | | |

OTHER PUBLICATIONS

International Search Report and Written Opinion of the International Searching Authority, International Patent Application No. PCT/US2013/028582, May 23, 2013.

* cited by examiner

*Primary Examiner* — David E Bochna
(74) *Attorney, Agent, or Firm* — Vinson & Elkins LLP

(57) ABSTRACT

A fitting assembly is provided having a nut and a ferrule, which in certain embodiments may be assembled by an operator. The nut and ferrule of the fitting assembly have passageways therethrough for receiving and removably holding tubing. The nut and ferrule fitting assembly may be adapted for use with a flat bottom port, such as in an analytical instrument, like liquid chromatography, gas chromatography, ion chromatography, or in in vitro diagnostic systems.

19 Claims, 9 Drawing Sheets

FLAT BOTTOM FITTING ASSEMBLY

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to an assembly for use in connecting tubing and other components of gas chromatography, liquid chromatography, in vitro diagnostic analysis systems, environmental (water) analysis systems, and other analytical systems, and relates more particularly to a reusable assembly well-suited for allowing quick connections and disconnections of tubing and other components in analytical systems.

2. Description of the Related Art

Liquid chromatography (LC), ion chromatography (IC) and gas chromatography (GC) are well-known techniques for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample. Additionally, LC systems may utilize mass spectrometric detection for identification and quantification of the sample, either in addition to, or as an alternative to, the conventional detectors described previously. Ion chromatography relies on the detection of ions in solution, so most metallic materials in the flow path can create interference in the detection scheme, as they create background ions.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, and then connect a supply of the selected mobile phase and a selected column to the LC system before operation. In order to be suitable for LC applications, each connection must be able to withstand the typical operating pressures of the LC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections in LC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples, and cannot be routinely used for ion chromatography. For example, the components in a sample may attach themselves to the wall of stainless steel tubing. This presents problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for "biocompatible" or "metal-free" connections through the use of a material that is chemically inert with respect to such "biological" samples and the mobile phase used with such samples, so that ions will not be released by the tubing and thus contaminate the sample.

In many applications using selector/injector valves to direct fluid flows, and in particular in liquid chromatography, the volume of fluids is small. This is particularly true when liquid chromatography is being used as an analytical method as opposed to a preparative method. Such methods often use capillary columns and are generally referred to as capillary chromatography. In capillary chromatography, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

As noted, liquid chromatography (as well as other analytical) systems typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the LC column itself; and a detector that analyzes the carrier fluid as it leaves the column. Ion chromatography may also utilize a suppressor column to facilitate detection dynamic range. These various components may typically be connected by a miniature fluid conduit, or tubing, such as metallic or polymeric tubing (for ion chromatography), usually having an internal diameter of 0.003 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. In addition, the use of such approaches to connect components of an LC system often results in deformation or swaging of a ferrule used to provide a leak proof seal of tubing to a fitting or component. This often means that the ferrule and tubing connection, once made, cannot be reused without a risk of introducing dead volumes into the system. In addition, such approaches may involve crushing or deformation of the inner diameter of the tubing, which may adversely affect the flow characteristics and the pressures of the fluid within the tubing.

Another approach to provide a connection in an LC system involves providing a fitting assembly that uses a combination of components, including two separate ferrules. Such an approach is considered undesirable because by requiring two places for the ferrules to provide leak proof seals, it provides two places where the fluid to be analyzed may leak, as well as where dead volumes may be provided. In addition, this approach involves the use of additional components, which can cost more and also increase the time and effect to assemble them to make a connection or disassemble them when disconnecting tubing from a component or other fitting assembly.

It will be understood by those skilled in the art that, as used herein, the term "LC system" is intended in its broad sense to include all apparatus and components in a system used in connection with liquid, ion, or gas chromatography, or in vitro diagnostic or environmental analysis, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Although the following discussion focuses on liquid chromatography, those skilled in the art will appreciate that much of what is said also has application to other types of AI systems and methods.

Therefore, it is an object of the present invention to provide a fitting with a ferrule or reversed lock ring for use in an LC or other AI system.

It is another object of the present invention to provide a fitting with a ferrule or reversed lock ring that can be reusable about 5 to 10 times or more.

It is another object of the present invention to provide a two component fitting assembly that performs like a one-piece fitting.

It is another object of the present invention to provide a mechanism allowing an operator to quickly disconnect or connect tubing or other component of an LC or other AI system.

It is another object of the present invention to provide a mechanism to reduce inefficiency and wasted time in connecting or disconnecting tubing or other component of an LC or other AI system.

It is yet another object of the present invention to provide a mechanism to allow an operator to quickly replace tubing or other component of an LC or other AI system.

It is yet another object of the present invention to provide a mechanism to allow an operator to quickly and easily achieve a leak-free connection of tubing or other component of an LC or other AI system by hand.

It is still another object of the present invention to provide a mechanism to minimize the risk of leakage or damage to the tubing of an LC system.

It is still another object of the present invention to provide a biocompatible assembly to allow an operator to quickly and easily achieve a biocompatible connection of tubing or other component of an LC or other AI system.

It is still another object of the present invention to provide a "metal-free" assembly to allow an operator to quickly and easily achieve a metal-free connection of tubing or other component of an LC or other AI system system.

The above and other advantages of the present invention will become readily apparent to those skilled in the art from the following detailed description of the present invention, and from the attached drawings, which are briefly described below.

SUMMARY OF THE INVENTION

The present disclosure overcomes one or more of the deficiencies of the prior art by providing fitting assemblies with a ferrule or reversed lock ring that are well-suited for use in liquid chromatography and other analytical instrument systems.

The present disclosure provides a fitting assembly for use in an analytical instrument system, comprising a nut having a first end and a second end and a passageway therethrough, a nut head proximal to the first end of the nut, an externally threaded portion, an external lip, and a first externally tapered portion proximal to the second end of the nut, and a ferrule having a first end, a second end, an internal lip proximal to the first end of the ferrule, and a passageway therethrough, wherein the passageway of the ferrule comprises an internally tapered portion proximal to the second end of the ferrule, and wherein the internal lip of the ferrule is adapted to securely engage with the external lip of the nut. A portion of the nut head, or the entire nut head can comprise a plurality of splines. The second end of the ferrule can be generally flat or planar.

The second end of the nut can have a number of additional features. For example, the nut can further comprise a second externally tapered portion between the externally threaded portion and the external lip, a first non-tapered portion between the second externally tapered portion and the external lip, a third externally tapered portion between the external lip and the first externally tapered portion, a first non-tapered portion between the externally threaded portion and the external lip and/or a second non-tapered portion between the third externally tapered portion and the first externally tapered portion, or any combination thereof The angle of the third externally tapered portion of the nut is generally between about 70° and about 90° included angle. Thus, the angle of the third externally tapered portion of the nut can be about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89° or 90° included angle.

The ferrule can also have additional features. For example the ferrule can further comprise an internally non-tapered portion between the internal lip and the internally tapered portion. The angle of the internally tapered portion of the ferrule is generally between about 80° and about 100° included angle. Therefore the angle of the internally tapered portion of the ferrule can be about 80°, about 81°, about 82°, about 83°, about 84°, about 85°, about 86°, about 87°, about 88°, about 89°, about 90°, about 91°, about 92°, about 93°, about 94°, about 95°, about 96°, about 97°, about 98°, about 99° or about 100° included angle.

The nut and/or the ferrule can comprise a number of different materials, including, but not limited to, a polymer such as polyetheretherketone, TEFLON®, TEFZEL®, DELRIN®, polyphenylene sulfide (PPS), polypropylene, or other high performance or commodity grade plastics or a metal such as stainless steel, or any combination thereof. In addition, the polymers may be reinforced with carbon, carbon fibers, glass fibers, steel fibers, or any combination thereof.

Additionally, the fitting assembly can comprise at least one tube extending through the passageways of the nut and the ferrule. The tube can comprise fluorinated ethylene propylene (FEP), perfluoroalkoxy (PFA), PEEK, PEEKsil™, stainless steel, fused silica, or any combination thereof. Furthermore, the fitting assembly can be used in a liquid chromatography, gas chromatography, or ion chromatography system, or in certain in vitro systems, including, but not limited to, an in vitro diagnostic analysis or environmental analysis system.

Therefore, the present disclosure also provides an analytical instrument system comprising at least one fitting assembly having a nut having a first end and a second end and a passageway therethrough, a nut head proximal to the first end of the nut, an externally threaded portion, an external lip, and a first externally tapered portion proximal to the second end of the nut, and a ferrule having a first end, a second end, an internal lip proximal to the first end of the ferrule, and a passageway therethrough, wherein the passageway of the ferrule comprises an internally tapered portion proximal to the second end of the ferrule, and wherein the internal lip of the ferrule is adapted to securely engage with the external lip of the nut. The analytical instrument system can comprise a liquid chromatography, gas chromatography, ion chromatography, in vitro diagnostic analysis or environmental analysis system. The end of the ferrule that is inserted into the port of the analytical instrument system can be generally flat or planar. In certain embodiments an operator can attach the fitting assembly to the analytical instrument system by hand, without the use of tools such as a wrench.

Furthermore, the present disclosure provides a method of connecting tubing in an analytical instrument system comprising connecting a fitting assembly comprising a tube extending therethrough to a port, fitting or component of the analytical instrument system; wherein the fitting assembly comprises a nut having a first end and a second end and a passageway therethrough, a nut head proximal to the first end of the nut, an externally threaded portion, an external lip, and a first externally tapered portion proximal to the second end of the nut, and a ferrule having a first end, a second end, an internal lip proximal to the first end of the ferrule, and a passageway therethrough, wherein the passageway of the ferrule comprises an internally tapered portion proximal to the second end of the ferrule, and wherein the internal lip of the ferrule is adapted to securely engage with the external lip of the nut, wherein the port, fitting or component comprises a first end, an internally threaded portion, and an internal tapered portion, a second end and a passageway therethrough, and wherein the internally threaded portion of the port, fitting or component is adapted to securely engage with the externally threaded portion of the nut. The end of the ferrule that is engaged in the port, fitting or component can be generally flat or planar.

These and other embodiments and advantages of the disclosed fitting assemblies are described below.

DETAILED DESCRIPTION

Figure 1:
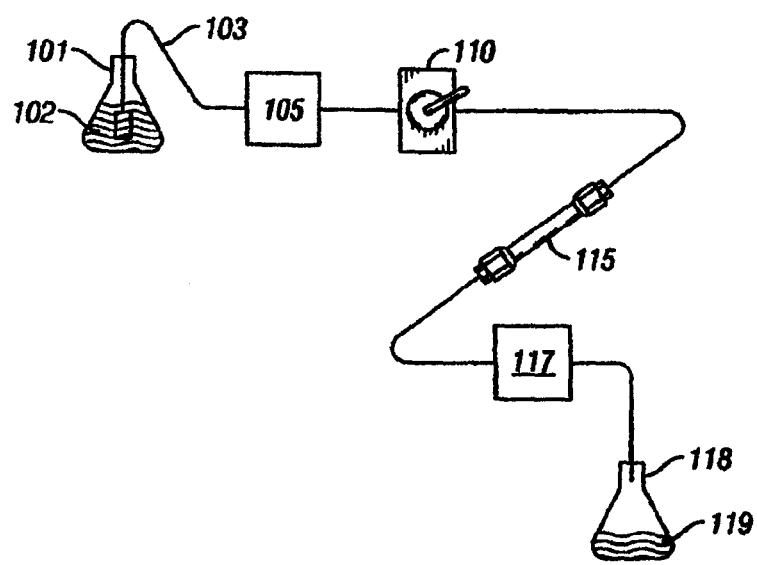
FIG. 1 is a block diagram of a conventional liquid chromatography system.

In FIG. 1, a block diagram of the essential elements of a conventional liquid chromatography (LC) system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well-known in the art, as is shown and described in U.S. Pat. No. 5,472,598, issued Dec. 5, 1995 to Schick, which is hereby incorporated by reference as if fully set forth herein. Those skilled in the art will also appreciate that while the discussion herein focuses on a LC system, other analytical systems can be used in connection with various embodiments of the invention, such as a mass spectrometry, microflow chromatography, nanoflow chromatography, nano-scale liquid chromatography, capillary electrophoresis, or reverse-phase gradient chromatography system.

Preferably, for an LC system to be biocompatible, the various components (except where otherwise noted) that may come into contact with the effluent or sample to be analyzed are made of the synthetic polymer polyetheretherketone, which is commercially available under the trademark PEEK™ from VICTREX®. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications.

Figure 2:
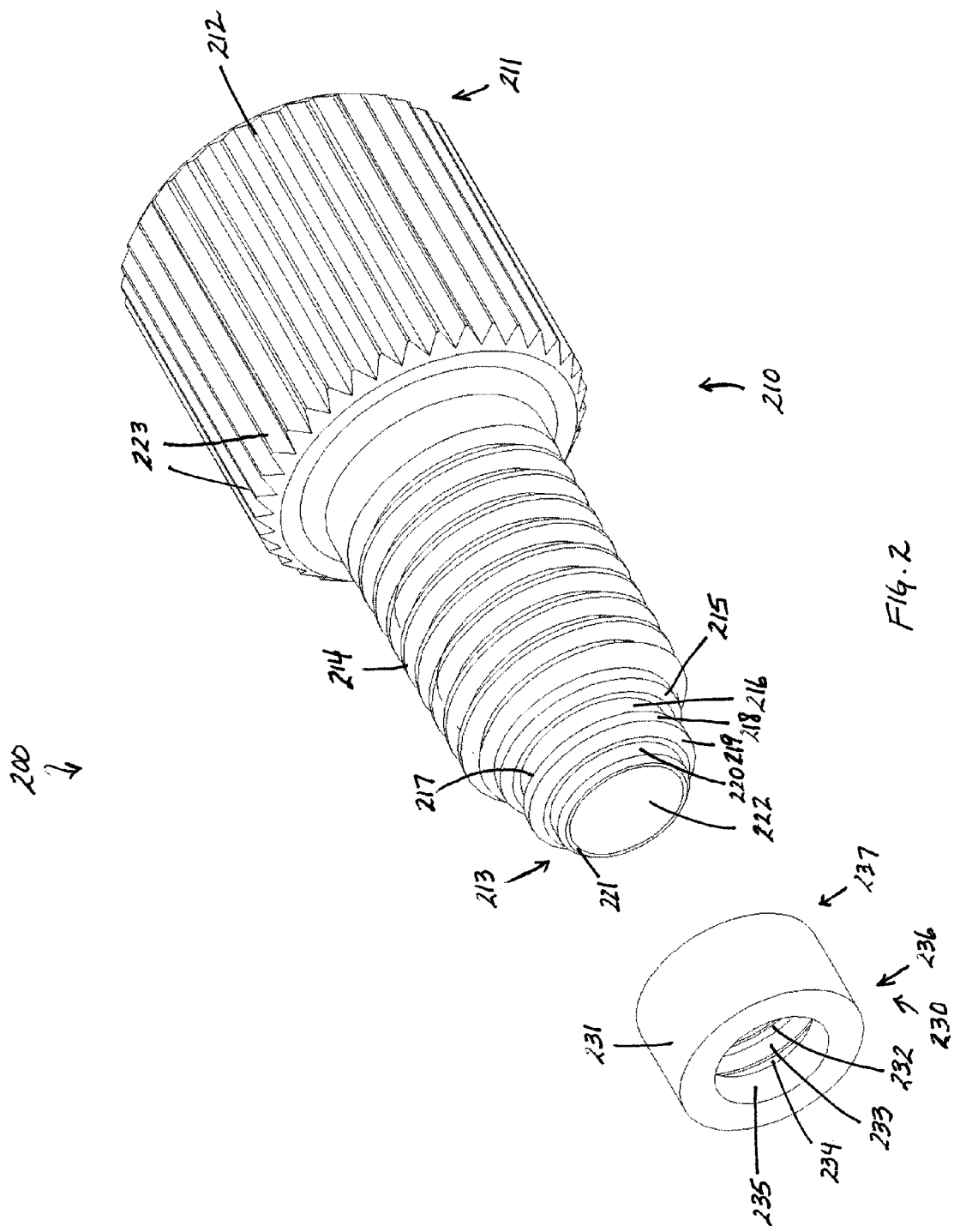
FIG. 2 is an exploded isometric view of various components of an embodiment of a fitting assembly in accordance with one aspect of the present invention.

Referring now to FIG. 2, a first embodiment of a fitting assembly 200 is shown. As shown in FIG. 2, the assembly 200 includes a nut 210 and a ferrule or reversed lock ring 230. Nut 210 comprises nut head 212, which is proximal to the first end 211 of the nut 210. An externally threaded portion 214 is between the first end 211 and the other or second end 213 of the nut 210, more proximal to the second end 213 of the nut 210. Nut 210 also comprises first externally tapered portion 215, first non-tapered portion 216, lip 217, second non-tapered portion 218, second externally tapered portion 219, third non-tapered portion 220, third externally tapered portion 221 and passageway 222 through nut 210. Ferrule 230 comprises first end 236, second end 237, externally non-tapered portion 231, internal lip 232, internally non-tapered portion 233, internally tapered portion 234, and passageway 235 through the ferrule 230. As shown in FIG. 2, the first end 236 of the ferrule 230 is generally flat or planar, and nut 210 and ferrule 230 are preferably circular and symmetric about a center axis. Those skilled in the art will realize that a circular shape has advantages, but the outer diameters in particular of nut head 212 may have a non-circular shape if desired, such as having flat or concave surface portions, to allow an operator to more easily grip and rotate nut 210. In addition, although a plurality of splines 223 are shown on nut head 212 in FIG. 2, the number and presence of such splines are optional, as is the circular design of nut head 212. As detailed herein, the externally threaded portion 214 of the nut 210 is adapted to be removably secured to a corresponding threaded portion of a port, a fitting, or a component of an LC or other analytical instrument (AI) system (not shown). Those skilled in the art will appreciate that the externally threaded portion 214 of the nut 210 may be adapted so that it can be removably engaged with any sized port, fitting, or component of an LC or other AI system (not shown). The use of external threads on one element, such as the nut 210, versus internal threads, is a matter of selection. Those skilled in the art will therefore appreciate that the nut 210 in an alternative embodiment could have internal threads (not shown) located near a second end that could be engaged with external threads (not shown) located near the first end of an alternative embodiment of a port, fitting, or component of an LC or AI system (not shown).

Still referring to FIG. 2, it can be seen that the first externally tapered portion 215, second externally tapered portion 219 and third externally tapered portion 221 of the nut 210, and the internally tapered portion 234 of the ferrule 230 each form a truncated conical shape. As shown in FIG. 2, the first externally tapered portion 215, second externally tapered portion 219 and third externally tapered portion 221 of the nut 210 each define an angle from the axis of the nut 210, and the internally tapered portion 234 of the ferrule 230 defines an angle from the axis of the ferrule 230. However, those skilled in the art will appreciate that the first externally tapered portion 215, second externally tapered portion 219 and third externally tapered portion 221 of the nut 210, and the internally tapered portion 234 of the ferrule 230 can define a different angle if desired, and can define angles that are about equal to each other, or differ from each other, depending upon the particular application. As detailed herein, the third externally tapered portion 221 of the nut 210 is adapted to be removably received in the internally tapered portion 234 of the passageway 235 through ferrule 230, and the non-tapered end 231 of the ferrule 230 is adapted to be removably received in a port, fitting, or component of a LC or AI system (not shown in FIG. 2; see FIG. 5).

Figure 3:
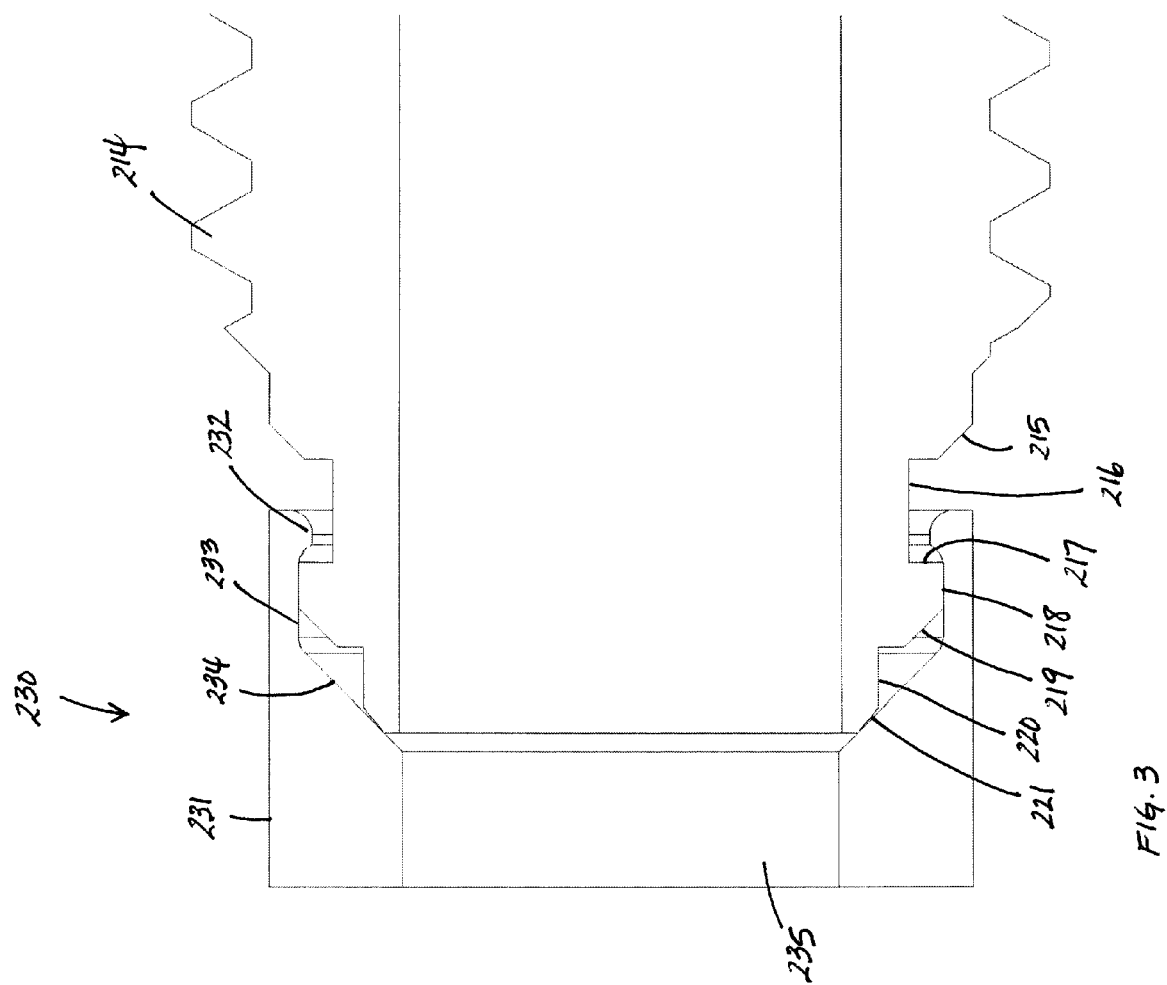
FIG. 3 is a cross-sectional view of the fitting assembly of FIG. 2 when assembled.

FIG. 3 shows a cross-sectional view of a portion of the fitting assembly 200 shown in FIG. 2 upon assembly. Like features and elements in the drawings have the same numerals in the various figures. Shown in FIG. 3 is a portion of the externally threaded portion 214, first externally tapered portion 215, first non-tapered portion 216, lip 217, second non-tapered portion 218, second externally tapered portion 219, third non-tapered portion 220, third externally tapered portion 221 and passageway 222 through nut 210, and ferrule 230 comprising first end 236, second end 237, externally non-tapered portion 231, internal lip 232, internally non-tapered portion 233, internally tapered portion 234, and passageway 235 through the ferrule 230. Visible in FIG. 3 is the position of the third externally tapered portion 221 of the nut 210 and the internally tapered portion 234 of the ferrule 230. Upon assembly internal lip 232 of ferrule 230 acts to keep nut 210 and ferrule 230 engaged through interaction with lip 217 of nut 210.

It will be appreciated that the nut 210 and ferrule 230 can comprise a number of different materials. For example, nut 210 and/or ferrule 230 in fitting assembly 200 can comprise a metal, such as stainless steel, or each can comprise a different material, such as a polymer. For example, the fitting assembly 200 can comprise a nut 210 comprising a polymer, such as polyetheretherketone (PEEK), and a ferrule 230 comprising stainless steel. It will be appreciated that a variety of metals and polymers may be selected for either nut 210 or ferrule 230 depending on the particular application, as that may involve a particular type of sample, a particular type of solvent, and/or a particular pressure range. In addition, the selection of materials for the tubing, such as fluorinated ethylene propylene (FEP), perfluoroalkoxy (PFA), PEEK, PEEKsil™, stainless steel, or fused silica, may lead to a selection of a particular material for nut 210 and/or ferrule 230. In addition, PEEK (or other polymers) may be used that is reinforced with carbon, carbon fibers, glass fibers, or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will further appreciate that fitting assembly 200 is shown as a fitting connection for connecting tubing to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

In certain applications utilizing PEEK, the PEEK used in fabrication of the nut 210, ferrule 230, and/or tubing (not shown) may be annealed according to manufacturer's recommendations. In general, the PEEK is ramped from about 70° F. to between about 300° F. and about 320° F. over about 40 to about 60 minutes, held at about 300° F. to about 320° F. for about 150 to about 180 minutes, ramped from between about 300° F. and about 320° F. to between about 392° F. and about 560° F. over about 90 minutes to about 300 minutes, held between about 392° F. and about 560° F. for between about 240 minutes and about 2880 minutes, and ramped down to between about 70° F. and about 284° F. over about 360 minutes to about 600 minutes. However, the skilled artisan will readily understand that different annealing protocols may be used in other applications.

In order for a fitting assembly to seal, it should generally remain in compression (relative to the surface of the port) throughout all environmental conditions. Therefore, in certain aspects a coating with a high coefficient of friction is applied to at least a portion of the internal passageway 222 of nut 210 and/or passageway 235 of ferrule 230 of the described fitting assembly 200. The high coefficient of friction between the outer surface of the tubing and the internal passageway 222 of nut 210 and/or passageway 235 of ferrule 230 of the described fitting assembly 200 keeps the tubing from extruding out of the port during pressurization, which results in increased burst pressure. In such embodiments the fitting connection or assembly 200 is coated at the internal surface of passageway 222 of nut 210 and/or the internal surface of passageway 235 of ferrule 230 that contacts the tubing starting at approximately 0.005 inches, about 0.0075 inches, about 0.01 inches, or about 0.02 inches from the tip of the fitting assembly 200. Coatings suitable for use with the presently described fitting connection or assembly include, but are not limited to, nickel, silica carbide, copper, and diamond coatings, and combinations thereof.

Figure 4:
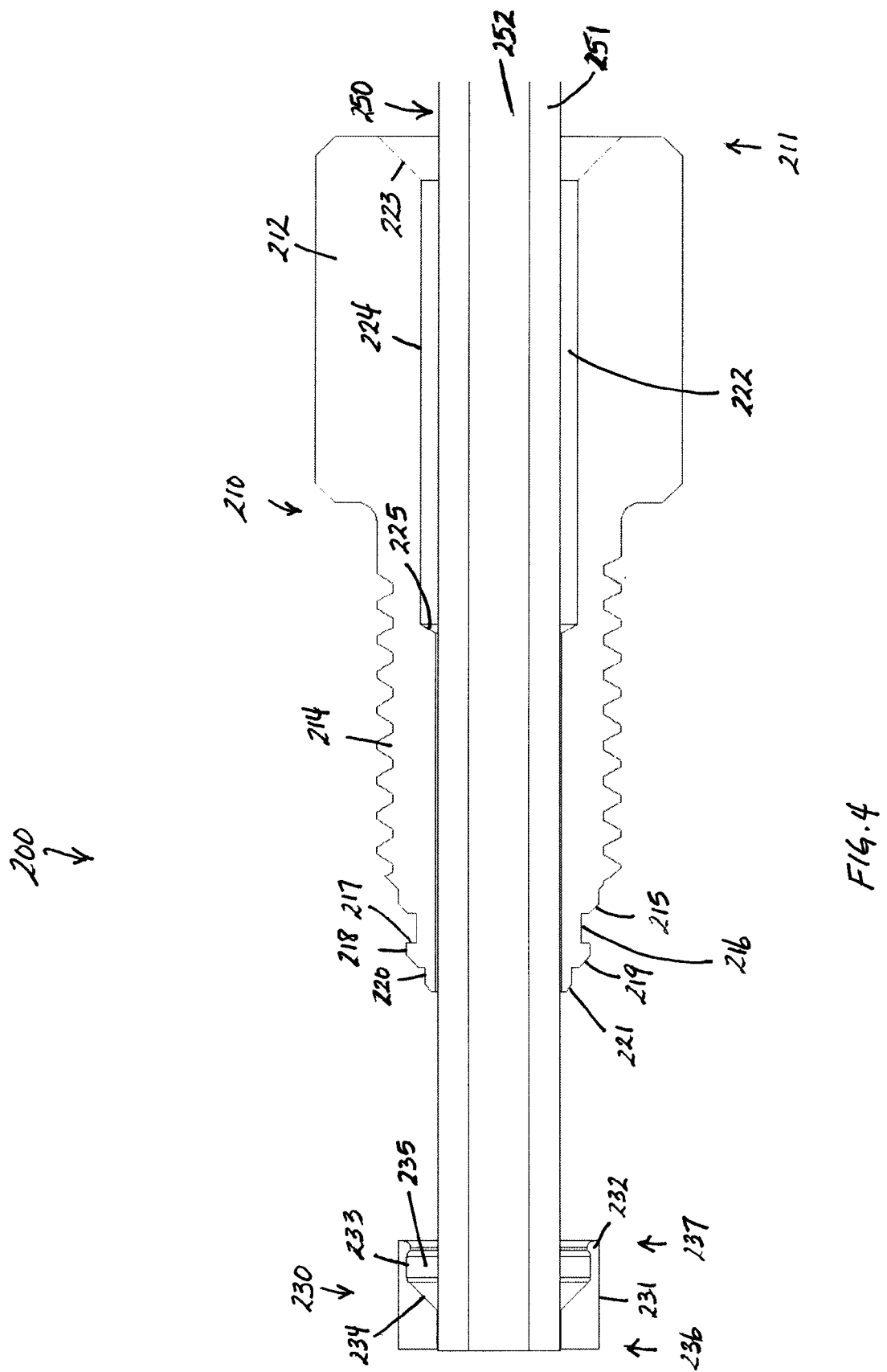
FIG. 4 is a cross-sectional view of the disassembled fitting assembly of FIG. 2 engaged with tubing.

FIG. 4 shows a cross-sectional view of the fitting assembly 200 shown in FIG. 2 with a piece of tubing 250 placed in the passageway 222 of the nut 210 and passageway 235 of the ferrule 230. As described previously nut 210 comprises nut head 212, which is proximal to the first end 211 of the nut 210. An externally threaded portion 214 is between the first end 211 and the other or second end 213 of the nut 210, more proximal to the second end 213 of the nut 210. Nut 210 also comprises first externally tapered portion 215, first non-tapered portion 216, lip 217, second non-tapered portion 218, second externally tapered portion 219, third non-tapered portion 220, third externally tapered portion 221 and passageway 222 through nut 210. Visible in FIG. 4 is first internally tapered portion 223, internal non-tapered portion 224, and second internally tapered portion 225. Ferrule 230 comprises first end 236, second end 237, externally non-tapered portion 231, internal lip 232, internally non-tapered portion 233, internally tapered portion 234, and passageway 235 through the ferrule 230. Tubing 250 comprises wall 251 and passageway 252.

Figure 5:
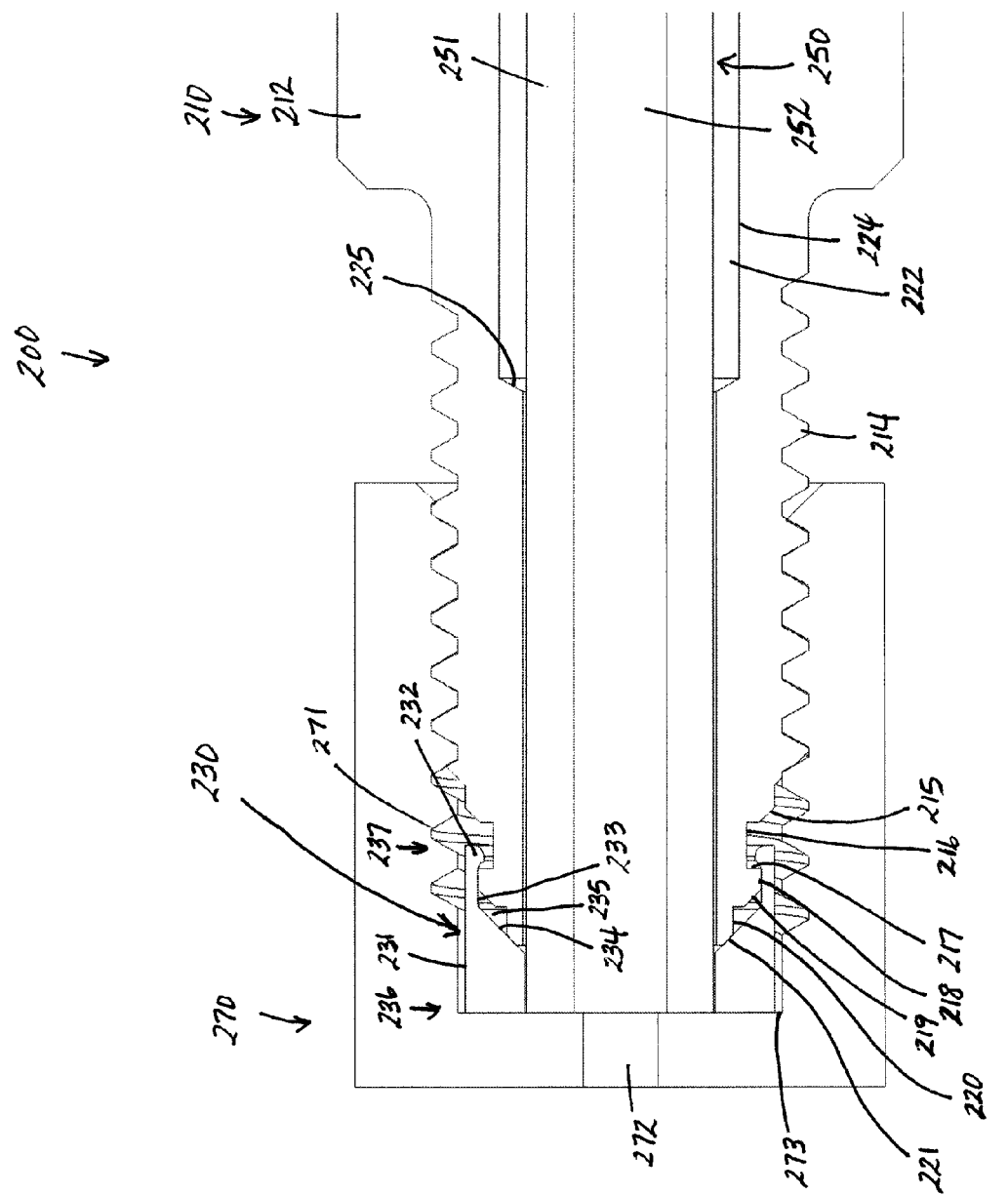
FIG. 5 is a cross-sectional view of the fitting assembly of FIG. 4 when assembled with tubing in a port.

FIG. 5 shows a cross-sectional view of a portion of the fitting assembly 200 shown in FIG. 4 upon assembly with a piece of tubing 250 placed in the passageway 222 of the nut 210 and passageway 235 of the ferrule 230 and the fitting assembly engaged in a port 270. As described previously nut 210 comprises nut head 212, externally threaded portion 214, first externally tapered portion 215, first non-tapered portion 216, lip 217, second non-tapered portion 218, second externally tapered portion 219, third non-tapered portion 220, third externally tapered portion 221 and passageway 222 through nut 210. Visible in FIG. 5 is internal non-tapered portion 224, and second internally tapered portion 225. Ferrule 230 comprises first end 236, second end 237, externally non-tapered portion 231, internal lip 232, internally non-tapered portion 233, internally tapered portion 234, and passageway 235 through the ferrule 230. Tubing 250 comprises wall 251 and passageway 252. Upon assembly internal lip 232 of ferrule 230 acts to keep nut 210 and ferrule 230 engaged through interaction with lip 217 of nut 210. Port 270 comprises internally threaded portion 271, passageway 272 and face 273. Fitting assembly 200 is engaged in port 270 through interaction of the externally threaded portion 214 of nut 210 of fitting assembly 200 and the internally threaded portion 271 of the port 270, with first end 236 of ferrule 230 and tubing 250 held flush against face 273 of the port 270.

Generally, the rotational force or torque applied to connect the nut 210, ferrule 230, and tubing 250 extending therethrough to a port 270 (or fitting, or other component in an LC or AI system, not shown) accomplishes two major tasks. First, the force of the connection of the fitting assembly 200 needs to be sufficient to provide a sealed and leak proof connection to the port 270 (or fitting or other LC or AI system component, not shown). In addition, the force of the connection of the fitting assembly 200 needs to be sufficient so that the tubing 250 is securely held and is sufficient to prevent detachment due to the hydraulic force of the fluid moving through the tubing 250. It is believed that the latter function typically involves greater forces than the former. It is believed that the fitting assembly 200 (such as shown in FIG. 2 through FIG. 5) provides an advantage in that it allows for better connections at higher pressures without requiring higher forces to connect fitting assembly 200, and without substantial deformation of the tubing.

Methods of using the fitting assembly 200 (such as shown in FIG. 2 through FIG. 5) are now described in further detail. Fitting assembly 200 can be provided to the operator with the nut 210 and the ferrule 230 pre-assembled. In one approach, the operator can insert a portion of the tubing through the passageways 222 and 235 of the pre-assembled nut 210 and ferrule 230. The operator can then engage the externally threaded portion 214 of the nut 210 with the internally threaded portion 271 of a port 270 (or fitting or other component of a LC or AI system, not shown). Once the externally threaded portion 214 of the nut 210 and the internally threaded portion 271 of the port 270 (or fitting or other component of a LC or AI system, not shown) begin to mate or engage, the operator then rotates the nut head 212 of the fitting assembly 200 relative to the port 270 (or fitting or other component of a LC or AI system, not shown), rotates the port 270 (or fitting or other component of a LC or AI system, not shown) relative to the nut head 212 of the fitting assembly 200, or rotates both the nut head 212 of the fitting assembly 200 and the port 270 (or fitting or other component of a LC or AI system, not shown) relative to each other. By so rotating the nut head 212 of the fitting assembly 200 and the port 270 (or fitting or other component of a LC or AI system, not shown) relative to one another, the operator drives the lip 217, second non-tapered portion 218, second externally tapered portion 219, third non-tapered portion 220, and third externally tapered portion 221 of the nut 210 further into the passageway 235 of the ferrule 230. In doing so, the operator thus forces the third externally tapered portion 221 of the nut 210 against the internally tapered portion 234 of the passageway 235 of the ferrule 230. In doing so, the third externally tapered portion 221 of the nut 210 is compressed and held firmly against the internally tapered portion 234 of the passageway 235 of the ferrule 230, thereby forming a leak-proof connection. Because the third externally tapered portion 221 of the nut 210 may be deformed or compressed as it is forced against the internally tapered portion 234 of the passageway 235 of the ferrule 230, a leak-proof connection may be obtained by the operator without the use of additional tools such as a wrench, pliers or the like, although tools, such as a torque wrench, may be used in certain applications. In one specific embodiment, when tubing having an outer diameter of 0.125 inches is used, the minimum diameter of the passageway in the fitting assembly can range between about 0.128 and about 0.130 inches.

Alternatively, an operator can first provide a nut 210 and ferrule 230, as well as tubing 250. In one approach, the operator can insert a portion of the tubing through the passageways 222 and 235 of the nut 210 and ferrule 230, respectively, in any order without assembling or otherwise connecting the nut 210 and ferrule 230. Next, the operator can insert the nut 210 into the ferrule 230 such that the lip 217 of the nut 210 engages and passes the internal lip 232 of the ferrule 230. The operator can then engage the externally threaded portion 214 of the nut 210 with the internally threaded portion 271 of a port 270 (or fitting or other component of a LC or AI system, not shown). Once the externally threaded portion 214 of the nut 210 and the internally threaded portion 271 of the port 270 (or fitting or other component of a LC or AI system, not shown) begin to mate or engage, the operator then rotates the nut head 212 of the fitting assembly 200 relative to the port 270 (or fitting or other component of a LC or AI system, not shown), rotates the port 270 (or fitting or other component of a LC or AI system, not shown) relative to the nut head 212 of the fitting assembly 200, or rotates both the nut head 212 of the fitting assembly 200 and the port 270 (or fitting or other component of a LC or AI system, not shown) relative to each other. By so rotating the nut head 212 of the fitting assembly 200 and the port 270 (or fitting or other component of a LC or AI system, not shown) relative to one another, the operator drives the lip 217, second non-tapered portion 218, second externally tapered portion 219, third non-tapered portion 220, and third externally tapered portion 221 of the nut 210 further into the passageway 235 of the ferrule 230. In doing so, the operator thus forces the third externally tapered portion 221 of the nut 210 against the internally tapered portion 234 of the passageway 235 of the ferrule 230. In doing so, the third externally tapered portion 221 of the nut 210 is compressed and held firmly against the internally tapered portion 234 of the passageway 235 of the ferrule 230, thereby forming a leak-proof connection. Because the third externally tapered portion 221 of the nut 210 may be deformed or compressed as it is forced against the internally tapered portion 234 of the passageway 235 of the ferrule 230, a leak-proof connection may be obtained by the operator without the use of additional tools such as a wrench, pliers or the like, although tools, such as a torque wrench, may be used in certain applications.

To disconnect a fitting assembly 200, such as shown in FIG. 2 through FIG. 5, an operator may either rotate the fitting assembly 200 relative to the port 270 (or fitting or other component of a LC or AI system, not shown), rotate the port 270 (or fitting or other component of a LC or AI system, not shown) relative to the fitting assembly 200, or rotate both the port 270 (or fitting or other component of a LC or AI system, not shown) and the fitting assembly 200 relative to each other. By rotating the port 270 (or fitting or other component of a LC or AI system, not shown) and/or the fitting assembly 200 relative to one another, the operator thus rotates the externally threaded portion 214 of nut 210 and the internally threaded portion 271 of the port 270 (or fitting or other component of a LC or AI system, not shown), respectively, and thereby disengages the connection between such threaded portions. At this point, the operator can use the assembly 200 and the leak-proof connection it provides, until the operator decides to remove the tubing 250 from the assembly 200. By selecting the direction of the threading of the externally threaded portion 214 of the nut 210 and internally threaded portion 271 of the port 270 (or fitting or other component of a LC or AI system, not shown), respectively, the operator can turn the entire fitting assembly 200 (when connected) by turning or rotating nut 210, such that the fitting assembly 200 rotates relative to the port 270 (or fitting or other component of a LC or AI system, not shown) and disengages therefrom. Thus, the entire fitting assembly 200 is easily disconnected from the port 270 (or fitting or other component of a LC or AI system, not shown).

Figure 6:
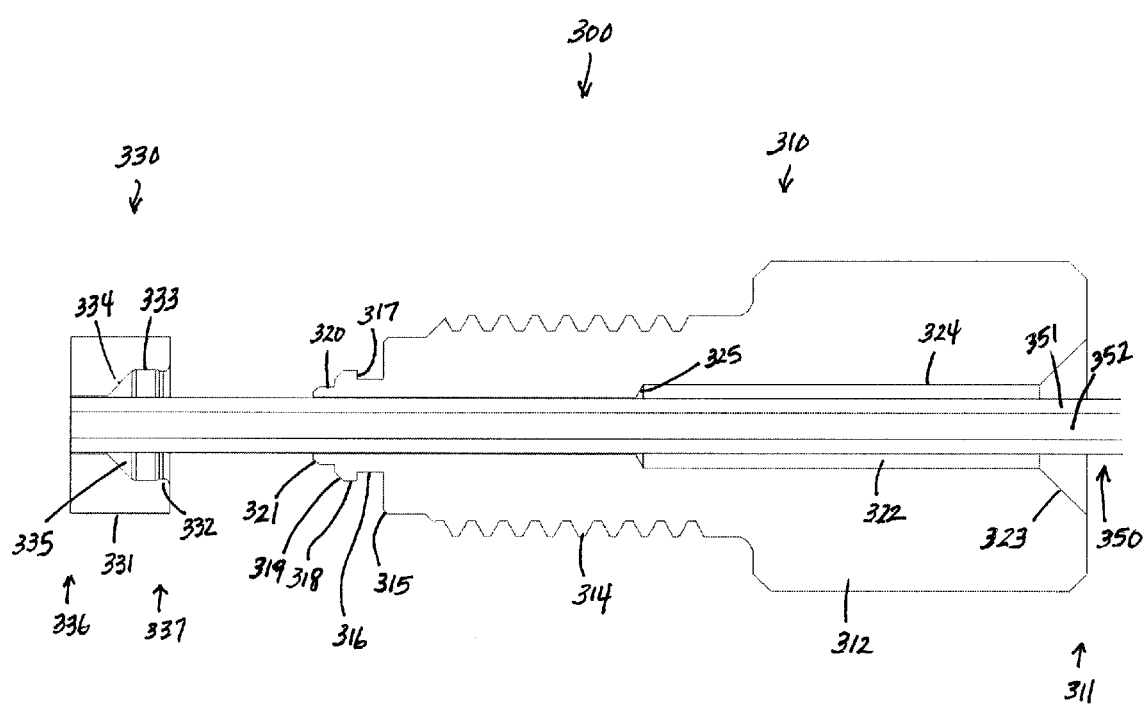
FIG. 6 is a cross-sectional view of a disassembled alternate embodiment of a fitting assembly in accordance with one aspect of the present invention engaged with tubing.

Referring now to FIG. 6, an cross-sectional view of an alternate embodiment of a fitting assembly 300 comprising nut 310 and ferrule 330 is shown with a piece of tubing 350 placed in the passageway 322 of the nut 310 and passageway 335 of the ferrule 330. Nut 310 comprises nut head 312, which is proximal to the first end 311 of the nut 310. An externally threaded portion 314 is between the first end 311 and the other or second end 313 of the nut 310, more proximal to the second end 313 of the nut 310. Nut 310 also comprises first externally tapered portion 315, first non-tapered portion 316, lip 317, second non-tapered portion 318, second externally tapered portion 319, third non-tapered portion 320, third externally tapered portion 321 and passageway 322 through nut 310. Visible in FIG. 6 is first internally tapered portion 323, internal non-tapered portion 324, and second internally tapered portion 325. Ferrule 330 comprises first end 336, second end 337, externally non-tapered portion 331, internal lip 332, internally non-tapered portion 333, internally tapered portion 334, and passageway 335 through the ferrule 330. Tubing 350 comprises wall 351 and passageway 352. As shown in FIG. 6, the first end 336 of ferrule 330 is generally flat or planar, and nut 310 and ferrule 330 are preferably circular and symmetric about a center axis. Those skilled in the art will realize that a circular shape has advantages, but the outer diameters in particular of nut head 312 may have a non-circular shape if desired, such as having flat or concave surface portions, to allow an operator to more easily grip and rotate nut 310. As detailed herein, the externally threaded portion 314 of the nut 310 is adapted to be removably secured to a corresponding threaded portion of a port, a fitting, or a component of an LC or other analytical instrument (AI) system (not shown; see FIG. 7). Those skilled in the art will appreciate that the externally threaded portion 314 of the nut 310 may be adapted so that it can be removably engaged with any sized port, fitting, or component of an LC or other AI system (not shown). The use of external threads on one element, such as the nut 310, versus internal threads, is a matter of selection. Those skilled in the art will therefore appreciate that the nut 310 in an alternative embodiment could have internal threads (not shown) located near a second end which could be engaged with external threads (not shown) located near the first end of an alternative embodiment of a port, fitting, or component of an LC or AI system (not shown).

Figure 7:
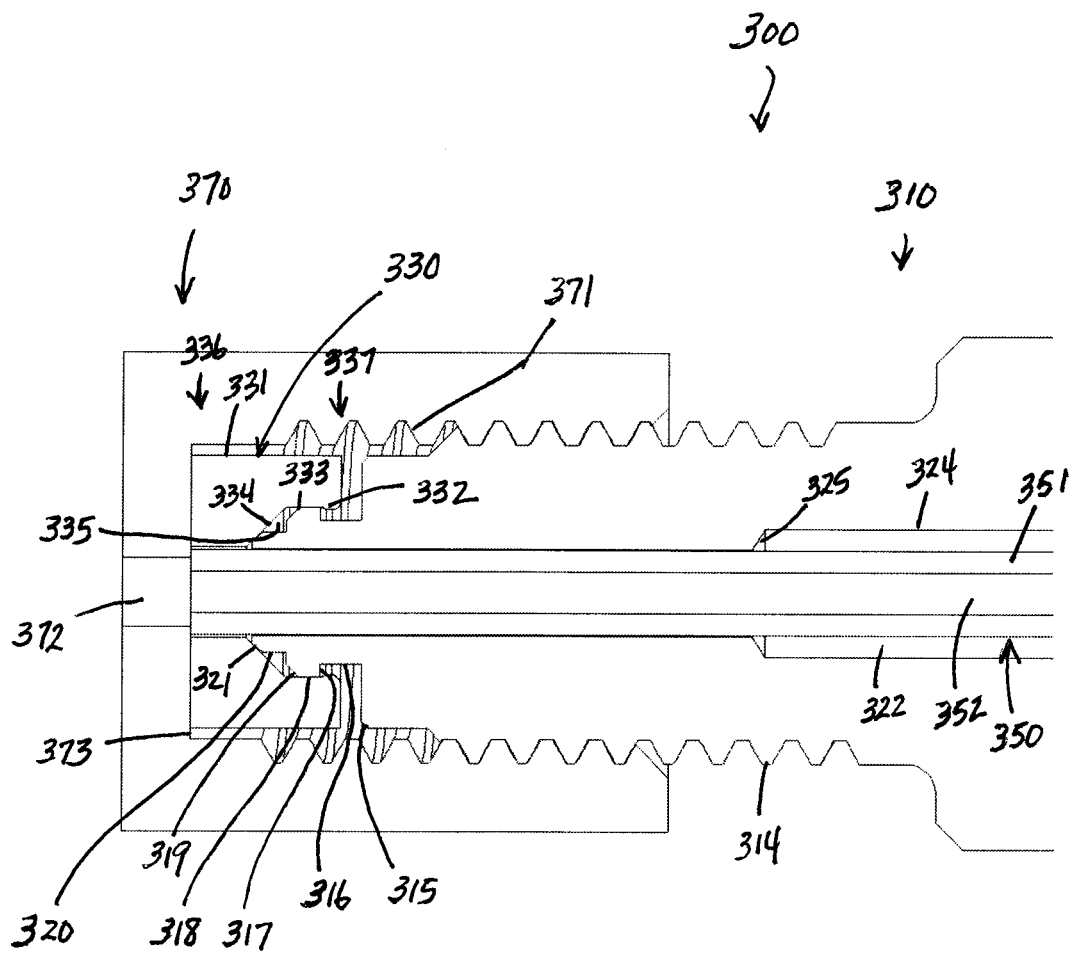
FIG. 7 is a cross-sectional view of the fitting assembly of FIG. 6 when assembled with tubing in a port.

FIG. 7 shows a cross-sectional view of a portion of the fitting assembly 300 shown in FIG. 6 upon assembly with a piece of tubing 350 placed in the passageway 322 of the nut 310 and passageway 335 of the ferrule 330 and the fitting assembly engaged in a port 370. As described previously nut 310 comprises nut head 312, externally threaded portion 314, first externally tapered portion 315, first non-tapered portion 316, lip 317, second non-tapered portion 318, second externally tapered portion 319, third non-tapered portion 320, third externally tapered portion 321 and passageway 322 through nut 310. Visible in FIG. 7 is internal non-tapered portion 324, and second internally tapered portion 325. Ferrule 330 comprises first end 336, second end 337, externally non-tapered portion 331, internal lip 332, internally non-tapered portion 333, internally tapered portion 334, and passageway 335 through the ferrule 330. Tubing 350 comprises wall 351 and passageway 352. Upon assembly internal lip 332 of ferrule 330 acts to keep nut 310 and ferrule 330 engaged through interaction with lip 317 of nut 310. Port 370 comprises internally threaded portion 371, passageway 372 and face 373. Fitting assembly 300 is engaged in port 370 through interaction of the externally threaded portion 314 of nut 310 of fitting assembly 300 and the internally threaded portion 371 of the port 370, with first end 336 of ferrule 330 and tubing 350 held flush against face 373 of the port 370.

The following example is included to demonstrate preferred embodiments of the invention. It should be appreciated by those of skill in the art that the techniques disclosed in the example which follows represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

Performance of a fitting assembly 200 as described herein, for example as shown in FIG. 2 through FIG. 5, was tested to examine the burst versus torque profile and the burst at assembly torque profile. In the burst versus torque and burst at assembly torque tests, fitting assemblies 200 similar to those shown in FIG. 2 through FIG. 5 were assembled, in which the nut 210 was made of PEEK and the ferrule 230 was made of PEEK. Fluorinated ethylene propylene (FEP) tubing was used in the tests. In the tests, a calibrated torque wrench was used to measure the torque applied to the test fitting assemblies. A standard union/adapter (1583-01; commercially available from IDEX Health and Science, Oak Harbor, Wash.) was used, as this was determined to be representative of actual use of the fitting assembly, and the burst pressure was measured.

Three trials of the burst versus torque test were performed. The torque range was broken into ten steps, and the results are shown below in Table 1 (Trial 1), Table 2 (Trial 2) and Table 3 (Trial 3).

TABLE 1

| Sample | Torque (inch-pounds) | Burst Pressure (psi) | Notes |
| --- | --- | --- | --- |
| 1 | 1.50 | 826 | Tube extruded from fitting |
| 2 | 2.00 | 1451 | None |
| 3 | 2.50 | 1437 | None |
| 4 | 3.00 | 1445 | None |
| 5 | 3.50 | 1418 | None |
| 6 | 4.00 | 1457 | None |
| 7 | 4.50 | 1458 | None |
| 8 | 5.00 | 1437 | None |
| 9 | 5.50 | 1438 | Ferrule stuck in port |
| 10 | 6.00 | 1385 | Tube extruded from fitting, ferrule stuck in port |

TABLE 2

| Sample | Torque (inch-pounds) | Burst Pressure (psi) | Notes |
| --- | --- | --- | --- |
| 1 | 1.50 | 349 | Tube extruded from fitting |
| 2 | 2.00 | 1423 | None |
| 3 | 2.50 | 1491 | None |

TABLE 2-continued

| Sample | Torque (inch-pounds) | Burst Pressure (psi) | Notes |
|---|---|---|---|
| 4 | 3.00 | 1440 | None |
| 5 | 3.50 | 1410 | None |
| 6 | 4.00 | 1451 | None |
| 7 | 4.50 | 1474 | None |
| 8 | 5.00 | 1447 | None |
| 9 | 5.50 | 1459 | None |
| 10 | 6.00 | 1462 | None |

TABLE 3

| Sample | Torque (inch-pounds) | Burst Pressure (psi) | Notes |
|---|---|---|---|
| 1 | 1.50 | 233 | Tube extruded from fitting |
| 2 | 2.00 | 1445 | None |
| 3 | 2.50 | 1488 | None |
| 4 | 3.00 | 1435 | None |
| 5 | 3.50 | 1451 | None |
| 6 | 4.00 | 1447 | None |
| 7 | 4.50 | 1466 | None |
| 8 | 5.00 | 1448 | Ferrule stuck in port |
| 9 | 5.50 | 1444 | None |
| 10 | 6.00 | 1445 | None |

Figure 8:
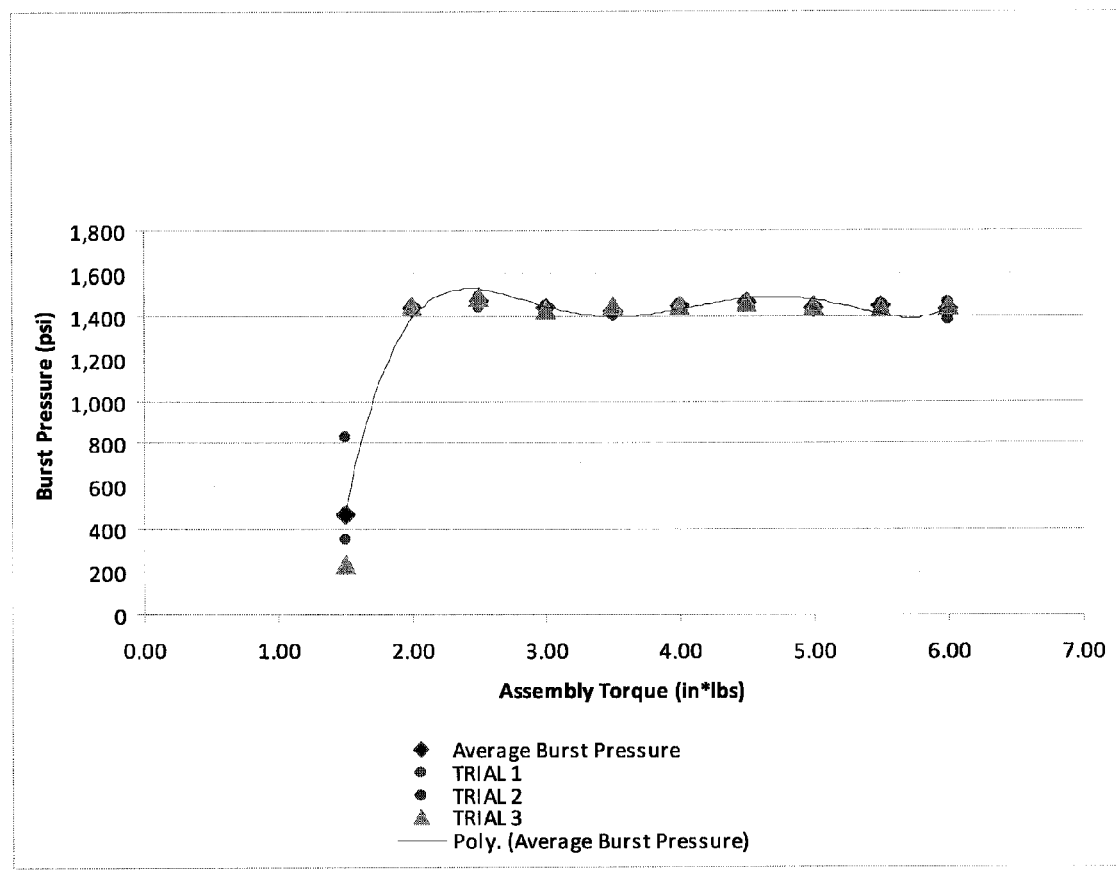
FIG. 8 is a graph showing the results of the burst versus torque tests conducted on fitting assemblies as described herein.

The results of the burst versus torque tests are shown graphically in FIG. 8. Based on the results of the burst versus torque tests, 2 inch-pounds of torque was used to seal the fitting assemblies for the burst at assembly torque test. A flow rate of 1 µl/minute was used in the burst at assembly torque test. The results of the burst at assembly torque test are shown in Table 4 below.

TABLE 4

| Sample | Torque (inch-pounds) | Burst Pressure (psi) | Notes |
|---|---|---|---|
| 1 | 2.00 | 1440 | None |
| 2 | 2.00 | 1442 | None |
| 3 | 2.00 | 1427 | None |
| 4 | 2.00 | 1427 | None |
| 5 | 2.00 | 1445 | None |
| 6 | 2.00 | 1460 | None |
| 7 | 2.00 | 1459 | None |
| 8 | 2.00 | 1447 | None |
| 9 | 2.00 | 1464 | None |
| 10 | 2.00 | 1464 | None |
| 11 | 2.00 | 1472 | None |
| 12 | 2.00 | 1461 | None |
| 13 | 2.00 | 1452 | None |
| 14 | 2.00 | 1124 | Weeping occurred |
| 15 | 2.00 | 1441 | None |
| 16 | 2.00 | 1466 | None |
| 17 | 2.00 | 1464 | None |
| 18 | 2.00 | 1474 | None |
| 19 | 2.00 | 1445 | None |
| 20 | 2.00 | 1472 | None |
| 21 | 2.00 | 1460 | None |
| 22 | 2.00 | 1331 | None |
| 23 | 2.00 | 1168 | Weeping occurred |
| 24 | 2.00 | 1461 | None |
| 25 | 2.00 | 1458 | Weeping occurred |
| 26 | 2.00 | 1426 | None |
| 27 | 2.00 | 1410 | None |
| 28 | 2.00 | 1445 | None |
| 29 | 2.00 | 1443 | None |
| 30 | 2.00 | 1429 | None |

Figure 9:
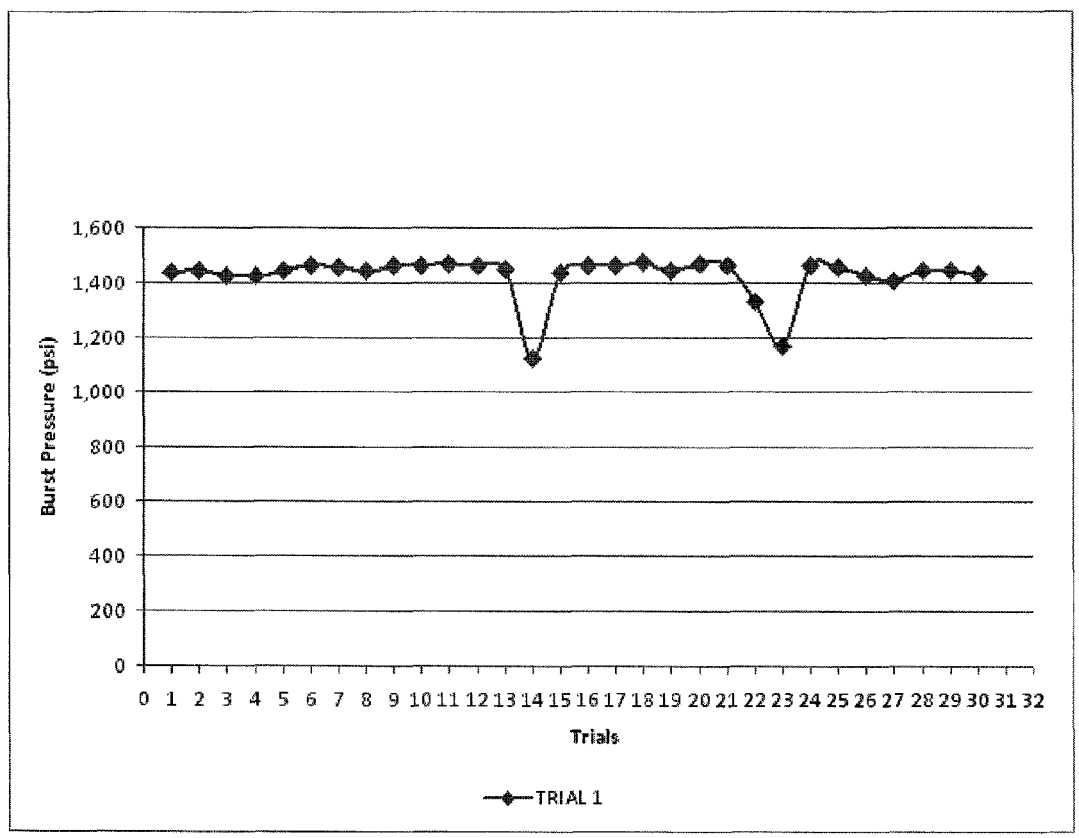
FIG. 9 is a graph showing the results of the burst at assembly torque tests conducted on fitting assemblies as described herein.

The results of the burst versus torque tests are shown graphically in FIG. 9. The fitting assemblies performed well, with a mean burst pressure of 1425.9 psi and a standard deviation of 80.9 psi.

While the present invention has been shown and described in various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

I claim:

1. A fitting assembly for use in an analytical instrument system, comprising:
   a) a nut having a first end and a second end and a passageway therethrough, a nut head proximal to said first end of the nut, an externally threaded portion, an external lip, a first externally tapered portion proximal to said second end of the nut, and a second externally tapered portion between said external lip and said first externally tapered portion; and
   b) a ferrule having a first end, a second end, an internal lip proximal to said first end of the ferrule, and a passageway therethrough, wherein said passageway of said ferrule comprises an internally tapered portion proximal to said second end of said ferrule, and wherein said internal lip of said ferrule is adapted to securely engage with said external lip of said nut.

2. The fitting assembly according to claim 1, wherein said nut head comprises a plurality of splines.

3. The fitting assembly according to claim 1, wherein said nut further comprises a third externally tapered portion between the externally threaded portion and the external lip.

4. The fitting assembly according to claim 3, wherein said nut further comprises a first non-tapered portion between said third externally tapered portion and said external lip.

5. The fitting assembly according to claim 4, wherein said nut further comprises a second non-tapered portion between said external lip and said second externally tapered portion.

6. The fitting assembly according to claim 5, wherein said nut further comprises a third non-tapered portion between said second externally tapered portion and said first externally tapered portion.

7. The fitting assembly according to claim 1, wherein the angle of said second externally tapered portion of said nut is between about 70° and 90° included angle.

8. The fitting assembly according to claim 7, wherein the angle of said second externally tapered portion of said nut is about 80° included angle.

9. The fitting assembly according to claim 1, wherein said ferrule further comprises an internally non-tapered portion between said internal lip and said internally tapered portion.

10. The fitting assembly according to claim 1, wherein the angle of said internally tapered portion of said ferrule is between about 80° and 100° included angle.

11. The fitting assembly according to claim 1, wherein the angle of said internally tapered portion of said ferrule is about 90° included angle.

12. The fitting assembly according to claim 1, wherein said nut or said ferrule comprises polyetheretherketone.

13. The fitting assembly according to claim 12, wherein said nut and said ferrule comprise polyetheretherketone.

14. The fitting assembly according to claim 1, further comprising at least one tube extending through the passageways of said nut and said ferrule.

15. The fitting assembly according to claim 1, wherein said analytical instrument system comprises a liquid chromatography, gas chromoatography, ion chromatography, in vitro diagnostic analysis or environmental analysis system.

16. An analytical instrument system comprising at least one fitting assembly having:
   a) a nut having a first end and a second end and a passageway therethrough, a nut head proximal to said first end of the nut, an externally threaded portion, an external lip, a first externally tapered portion proximal to said second end of the nut, and a second externally tapered portion between said external lip and said first externally tapered portion; and
   b) a ferrule having a first end, a second end, an internal lip proximal to said first end of the ferrule, and a passageway therethrough, wherein said passageway of said ferrule comprises an internally tapered portion proximal to said second end of said ferrule, and wherein said internal lip of said ferrule is adapted to securely engage with said external lip of said nut.

17. The analytical instrument system according to claim 16, wherein said analytical instrument system comprises a liquid chromatography, gas chromoatography or ion chromatography system.

18. The analytical instrument system according to claim 16, wherein said analytical instrument system comprises an in vitro diagnostic analysis or environmental analysis system.

19. A method of connecting tubing in an analytical instrument system comprising connecting a fitting assembly comprising a tube extending therethrough to a port, fitting or component of said analytical instrument system; wherein said fitting assembly comprises:
   a) a nut having a first end and a second end and a passageway therethrough, a nut head proximal to said first end of the nut, an externally threaded portion, an external lip, a first externally tapered portion proximal to said second end of the nut, and a second externally tapered portion between said external lip and said first externally tapered portion; and
   b) a ferrule having a first end, a second end, an internal lip proximal to said first end of the ferrule, and a passageway therethrough, wherein said passageway of said ferrule comprises an internally tapered portion proximal to said second end of said ferrule, and wherein said internal lip of said ferrule is adapted to securely engage with said external lip of said nut;

wherein said port, fitting or component comprises a first end, an internally threaded portion, and an internal tapered portion, a second end and a passageway therethrough, and wherein said internally threaded portion of said port, fitting or component is adapted to securely engage with said externally threaded portion of said nut.

* * * * *